United States Patent [19]

Zanno et al.

[11] Patent Number: 4,626,442

[45] Date of Patent: Dec. 2, 1986

[54] 3-HYDROXY-4-ALKYLOXYPHENYL HETEROCYCLIC AROMATIC CARBOXYLATES

[75] Inventors: Paul R. Zanno, Port Chester; Ronald E. Barnett, Suffern; Jed A. Riemer, Scarsdale, all of N.Y.

[73] Assignee: General Foods Corporation, White Plains, N.Y.

[21] Appl. No.: 842,345

[22] Filed: Mar. 21, 1986

Related U.S. Application Data

[62] Division of Ser. No. 566,633, Dec. 29, 1983.

[51] Int. Cl.⁴ ............................................. A23L 1/236

[52] U.S. Cl. .................................. 426/548; 426/576; 426/590; 426/579; 426/658; 426/804

[58] Field of Search ............... 426/658, 590, 548, 576, 426/804, 579

[56] References Cited

U.S. PATENT DOCUMENTS 4,410,702  10/1983  Postle et al. .......................... 549/71

Primary Examiner—Jeanette Hunter
Attorney, Agent, or Firm—Linn I. Grim; Thomas A. Marcoux; Daniel J. Donovan

[57] ABSTRACT

Novel 3-hydroxy-4-alkyloxyphenyl heterocyclic aromatic carboxylate compounds particularly well suited as sweeteners in foodstuff.

4 Claims, No Drawings

3-HYDROXY-4-ALKYLOXYPHENYL HETEROCYCLIC AROMATIC CARBOXYLATES

This is a division of application Ser. No. 566,633, filed 12-29-83.

BACKGROUND OF THE INVENTION

1. Field of the Invention

This invention relates to a novel group of compounds and more particular to a novel group of compounds particularly well suited as sweeteners in edible foodstuff.

2. Description of the Prior Art

Sweetness is one of the primary taste cravings of both animals and humans. Thus, the utilization of sweetening agents in foods in order to satisfy this sensory desire is well established.

Naturally occurring carbohydrate sweeteners such as sucrose, are still the most widely used sweetening agents. While these naturally occurring carbohydrates, i.e., sugars, generally fulfill the requirements of sweet taste, the abundant usage thereof does not occur without deleterious consequence, e.g., high caloric intake and nutritional imbalance. In fact, oftentimes the level of these sweeteners required in foodstuffs is far greater than the level of the sweetener that is desired for economic, dietic or other functional consideration.

In an attempt to eliminate the disadvantages concomitant with natural sweeteners, considerable reasearch and expense have been devoted to the production of artificial sweeteners, such as for example, saccharin, cyclamate, dihydrochalcone, aspartame, etc. While some of these artificial sweeteners satisfy the requirements of sweet taste without caloric input, and have met with considerable commercial success, they are not, however, without their own inherit disadvantages. For example, many of these artificial sweeteners have the disadvantages of high cost, as well as delay in the perception of the sweet taste, persistent lingering of the sweet taste, and a very objectionable bitter, metallic aftertaste when used in food products.

Since it is believed that many disadvantages of artificial sweeteners, particularly aftertaste, is a function of the concentration of the sweetener, it has been previously suggested that these effects could be reduced or eliminated by combining artificial sweeteners such as saccharin, with other ingredients or natural sugars, such as sorbitol, dextrose, maltose etc. These combined products, however, have not been entirely satisfactory either. Some U.S. Patents which disclose sweetener mixtures include for example, U.S. Pat. No. 4,228,198; U.S. Pat. No. 4,158,068; U.S. Pat. No. 4,154,862; U.S. Pat. No. 3,717,477.

Also much work has continued in an attempt to develop and identify compounds that have a sweet taste. For example, in Yamato, et al., Chemical Structure and Sweet Taste Of Isocoumarin and Related Compounds, Chemical Pharmaceutical Bulletin, Vol. 23, p. 3101–3105 (1975) and in Yamato et al. Chemical Structure and Sweet Taste Of Isocoumarins and Related Compound, Chemical Senses And Flavor, Vol. 4 No. 1, p. 35–47(1979) a variety of sweet structures are described. For example, 3-Hydroxy-4-methoxybenzyl phenyl ether is described as having a faint sweet taste.

Despite the past efforts in this area, research continues. Accordingly, it is desired to find a compound that provides a sweet taste when added to foodstuff or one which can reduce the level of sweetener normally employed and thus eliminate or greatly diminish a number of disadvantages associated with prior art sweeteners.

SUMMARY OF THE INVENTION

This invention pertains to sweetness compounds of the structure:

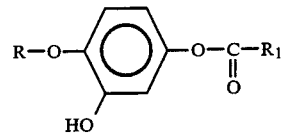

wherein:
R is selected from the group consisting of methyl and ethyl;
$R_1$ is selected from the group consisting of

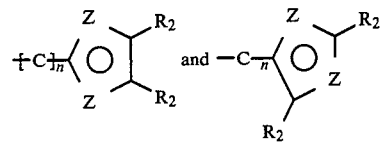

wherein n is an integer from 0 to 1;
each Z is selected from the group consisting of S, O, $NR_2$, N and $CR_2$ with the proviso that at least one Z is a hetero atom; and
each $R_2$ is selected from the group consisting of H, $CH_3$, $CH_2CH_3$, $CH_2CH_2CH_3$, $CH(CH_3)_2$, OH, $OCH_3$, $OCH_2CH_3$, $OCH(CH_3)_2$, $CH_2OH$, $CH_2CH_2OH$, $CH_2CHOHCH_3$, $CH_2OCH_3$, CHO, $COCH_3$, $COCH_2CH_3$, $CH_2COCH_3$, and $COOCH_3$ with the proviso that $R_1$ contain no more than 12 carbon atoms; and salts thereof.

Most of the compounds of the formula described hereinabove are sweeteners, the sweetness of which is many times that of comparable amounts of sucrose. The sweetness of compounds of the formula can be readily determined by a simple test procedure described herein.

Several compounds of the formula when tested for sweetness showed little, if any, sweetness to sucrose, whereas most compounds have greater sweetness than sucrose, e.g., 100–300 times greater. Compounds in which $R_1$ is 2-pyrrolecarboxylate and 3-pyrrolecarboxylate show no sweetness and are not within the preview of this invention. In general, the sweetener compound should possess a sweetness at least five times greater and preferably at least thirty times and more preferably 100 times greater than sucrose on comparable weight basis.

These compounds in addition to having a sweet taste, function as a low calorie sweetening agent when employed with a foodstuff.

DETAILED DESCRIPTION OF THE INVENTION

In accordance with the present invention, the novel compounds are selected from the group consisting of;

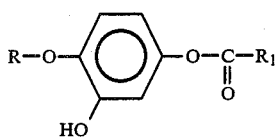

wherein:

R is selected from the group consisting of methyl and ethyl;

$R_1$ is selected from the group consisting of

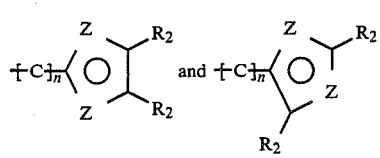

wherein n is an integer from 0 to 1;

Z is selected from the group consisting of S, O, $NR_2$, N and $CR_2$ with the proviso that at least one Z is a hetero atom; and $R_2$ is selected from the group consisting of H, $CH_3$, $CH_2CH_3$, $CH_2CH_2CH_3$, $CH(CH_3)_2$, OH, $OCH_3$, $OCH_2CH_3$, $OCH(CH_3)_2$, $CH_2OH$, $CH_2CHOHCH_3$, $CH_2OCH_3$, CHO, $COCH_3$, $COCH_2CH_3$, $CH_2COCH_3$, and $COOCH_3$ with the proviso that $R_1$ contain no more than 12 carbon atoms; and salts thereof.

Preferably $R_1$ will contain no more than 10 carbon atoms and more preferably will contain no more than 8 carbon atoms.

Illustrative compounds within the above formula include:

3-hydroxy-4-ethoxyphenyl 2-furoate
3-hydroxy-4-methoxyphenyl 2-furoate
3-hydroxy-4-methoxyphenyl 2-thiophenecarboxylate
3-hydroxy-4-methoxyphenyl 3-thiophenecarboxylate
3-hydroxy-4-methoxyphenyl 3-furoate
3-hydroxy-4-methoxyphenyl 5-methyl-2-furoate
3-hydroxy-4-methoxyphenyl 5-methyl-2-thiophenecarboxylate
3-hydroxy-4-methoxyphenyl 2-isopropyl-2-thiophenecarboxylate
3-hydroxy-4-methoxyphenyl 2-thienylacetate
3-hydroxy-4-methoxyphenyl N-acetyl-2-pyrrolecarboxylate
3-hydroxy-4-methoxyphenyl 5-acetal-2-thienoate
3-hydroxy-4-methoxyphenyl 5-methoxy-2-thiophenecarboxylate
3-hydroxy-4-methoxyphenyl 3,5-dimethyl-2-thiophenecarboxylate
3-hydroxy-4-methoxyphenyl 2-thiazolecarboxylate
3-hydroxy-4-methoxyphenyl 5-thiazolecarboxylate
3-hydroxy-4-methoxyphenyl 2-oxazolecarboxylate
3-hydroxy-4-methoxyphenyl 2-imidazolecarboxylate
3-hydroxy-4-methoxyphenyl 2-furylacetate
3-hydroxy-4-methoxyphenyl 2-pyrrylacetate These novel compounds are effective sweetness agents when used alone or in combination with other sweeteners in foodstuffs. For example, other natural and/or artificial sweeteners which may be used with the novel compounds of the present invention include sucrose, fructose, corn syrup solids, dextrose, xylitol, sorbitol, mannitol, acetosulfam, thaumatin, invert sugar, saccharin, cyclamate, dihydrochalcone, aspartame (L-aspartyl-L-phenylalanine methyl ester) and other dipeptides, glycyrrhizin and stevioside and the like.

Typical foodstuffs, including pharmaceutical preparations, in which the sweetness agents of the present invention may be used are, for example, beverages including soft drinks, carbonated beverages, ready to mix beverages and the like, infused foods (e.g. vegetables or fruits), sauces, condiments, salad dressings, juices, syrups, desserts, including puddings, gelatin and frozen desserts, like ice creams, sherbets and icings, confections, toothpaste, mouthwash, chewing gum, intermediate moisture foods (e.g. dog food) and the like.

In order to achieve the effects of the present invention, the compounds described herein are generally added to the food product at a level which is effective to perceive sweetness in the food stuff and suitably is in an amount in the range of from about 0.0001 to 2% by weight based on the consumed product. Greater amounts are operable but not practical. Preferred amounts are in the range of from about 0.0005 to about 1% of the foodstuffs. Generally, the sweetening effect provided by the present compound is experienced over a wide pH range, e.g. 2 to 10 preferably 3 to 7 and in buffered and unbuffered formulations.

It is preferred then when the compounds are used in the foodstuff that the compounds have a sucrose equivalent of at least 2 percent by weight, more preferrably that they have a sucrose equivalent of at least 5 percent by weight and most preferrably they have a sucrose equivalent of at least 8 percent by weight.

A taste procedure for determination of sweetness merely involves the determination of sucrose equivalency.

Sucrose equivalence for sweetener are readily determined. For example, the amount of a sweetener that is equivalent to 10 weight percent aqueous sucrose can be determined by having a panel of tasters taste the solution of a sweetener and match its sweetness to the standard solution of sucrose. Obviously, sucrose equivalents for other than 10 weight percent are determined by matching the appropriate sucrose solutions.

It is desired that when the sweetening agent of this invention is employed in combination with another sweetener the sweetness equivalence of the other sweetener is equal to or above about 2 percent sucrose equivalence. Preferably the combination of sweeteners provides a sucrose equivalence in the range of from about 3 weight percent to about 25 weight percent and most preferably 4 weight percent to about 15 weight percent.

In order to prepare the compounds of the present invention an esterification reaction is employed. A 3-benzyloxy-4-R-oxyphenol is esterified with an acid form or acid chloride form of the $R_1$ moiety (e.g. $R_1CO_2H$ or $R_1COCl$). This provides a 3-benzyloxy-4-R-oxyphenyl $R_1$-carboxylate. The 3-benzyloxy moiety is subsequently converted to the desired 3-hydroxy-4-R-oxyphenyl $R_1$-carboxylate.

For example, when R is methyl then 3-benzyloxy-4-methoxyphenol is used for the esterification reaction. To obtain 3-benzyloxy-4-methoxyphenol, isovanillin which is also known 3-hydroxy-4-methoxybenzaldehyde is used as a starting material. Isovanillin is a commercially available material. If R is to be other than methyl then the appropriate 4-alkoxy compound is used as the starting material. The 4-alkoxy compound is made by alkylation of 3,4-dihydroxybenzaldehyde which is commercially available. Isovanillin is converted to 3-benzyloxy-4-methoxybenzaldehyde which is then converted to 3-benzyloxy-4-methoxyphenyl formate by the following reactions.

Performic acid is prepared by first heating a mixture of 30% by weight hydrogen peroxide and 97% by weight formic acid in a weight ratio of 1:5 to 60° C. and then cooling the mixture in an ice both. The mixture is then added dropwise over a three hour period to an ice-cold 1M solution of 3-benzyloxy-4-methoxybenzaldehyde in methylene chloride. After the addition is completed a saturated solution of sodium bisulfite is added dropwise until the mixture exhibits a negative starch-iodide test for peroxides. The reaction mixture is poured into an equal volume of water. The phases separate and the aqueous phase is extracted with two parts of methylene chloride per part of aqueous phase. The combined organic phases are washed with water, dried over magnesium sulfate and the solvent is evaporated. The 3-benzyloxy-4-methoxyphenyl formate is recrystallized from 95% by weight ethanol.

The 3-benzyloxy-4-methoxyphenyl formate is then converted to 3-benzyloxy-4-methoxyphenol by the following reaction. A mixture of 3-benzyloxy-4-methoxyphenyl formate, methanol and 1M sodium hydroxide in a weight ratio of 1:6:10 is heated under reflux conditions for one hour, the mixture is allowed to cool and an equal volume of water is added. The solution is washed with ether and acidified to pH 3 with concentrated hydrochloric acid. The resulting mixture is extracted with ether. The combined extracts are washed with water and dried over magnesium sulphate and the solvent is evaporated to yield a tan solid which is 3-benzyloxy-4-methoxyphenol.

The 3-benzyloxy-4-methoxyphenol is reacted with the $R_1$ acid or the $R_1$ acid chloride according to one of the following reactions. When an $R_1$ acid is to be used, the phenol (1.0 equiv.), triethylamine (1.1 equiv.) and 4-dimethylaminopyridine (0.1 equiv.) are first dissolved in methylene chloride. The desired $R_1$ acid chloride (1.1 equiv.) is added and the mixture is stirred for 12 hours. The mixture is then washed with 1M hydrochloric acid, saturated sodium bicarbonate and water and dried over magnesium sulfate. The solvent is evaporated to yield the desired product which may be purified by chromotography if necessary.

If an $R_1$ acid is to be used then a solution of the phenol (1.0 equiv.), carboxylic acid (1.1 equiv.) and 4-dimethylaminopyridine (0.1 equiv.) in methylene chloride is first stirred at 0° C. Dicyclohexylcarbodiimide (1.1 equiv.) is added and the mixture allowed to warm slowly to room temperature overnight. The mixture is filtered to remove dicyclohexylurea. The filtrate is washed with 1M hydrochloric acid, saturated sodium bicarbonate and water and then is dried over magnesium sulfate. The solvent is evaporated to yield the desired product which may be purified by chromatography if necessary.

In order to obtain the desired product it is necessary to remove the benzyl protecting group. The benzyl group can be removed by one of two methods. In one method the benzyl protected compound is suspended in 95 percent ethanol and 10 percent palladium on carbon is added. The mixture is placed on a Parr hydrogenator which is then charged with hydrogen to a pressure of approximately 50 lbs. per square inch. Upon the cessation of hydrogen uptake (approximately 2-5 hours) the mixture is filtered through a Celite pad and the solvent evaporated to yield the desired product which may be purified by chromatography if necessary.

In another method of removing the benzyl protecting group a solution of the benzyl protected ester (1 equiv.) in methylene chloride is stirred at room temperature under argon atmosphere. Iodotrimethylsilane (1.3 equiv.) is added and the reaction mixture stirred for 12 hours. The reaction is then quenched with methanol and stirred for thirty minutes. The solvent is then evaporated and the residue dissolved in ether. This solution is washed with 1M hydrochloric acid, saturated sodium bicarbonate and water, dried over magnesium sulfate and the solvent is evaporated. The product is purified by column chromatography over silia gel.

Further details are described in McMurry et al. Journal Chemical Society, pages 1491–8 (1960) and Robinson et al. Journal Chemical Society, pages 3163–7 (1931).

The requisite acid or acid chloride forms of the desired $R_1$ moiety are either commercially available, known in the art, or prepared from commercially available starting materials by known synthetic procedures.

Commercially available carboxylic acid precursors can be found in, *Chem. Sources U.S.A.*, Directories Publishing Co., Inc. Ormond Beach, Fla. as well as *Chem. Sources Europe*, Chem. Sources Europe Publisher, Mountain Lakes, N.J.

Carboxylic acids, in general, can be prepared by a host of synthetic procedures from other available starting materials. Examples of these methods including specifics and reaction conditions can be found in, *Survey of Organic Synthesis*, Vols. 1 and 2, C. Buehler & D. Pearson, Wiley Interscience Inc., New York and *Advanced Organic Chemistry; Reactions, Mechanisms and Structure*, J. March, McGraw-Hill, New York.

In addition to these referenced methods carboxylic acids can be obtained by conversion of other chemical functionalities. A reference for the interconversion of chemical functionalities can be found in, *Compendium of Organic Synthetic Methods*, Vols. I & II, I. T. Harrison & S. Harrison, Wiley Interscience Inc., New York.

The present new compounds form salts due to the presence of the phenolic hydroxy group. Thus, metal salts can be formed by reaction with alkali such as aqueous ammonia, alkali and alkaline earth metal compounds such as sodium, potassium and calcium oxides, hydroxides, carbonates and bicarbonate. The salts are of higher aqueous solubility than the parent compound and are useful for purification or isolation of the present products.

The following examples are presented to further illustrate this invention.

EXAMPLE I

The compound 3-hydroxy-4-methoxyphenyl 2-furoate was made as follows. An amount of 2.00 gms. of 3-benzyloxy-4-methoxyphenol, 1.00 gms. of triethylamine and 0.10 gms of 4-dimethylaminopyridine were dissolved in 100 ml. of methylene chloride at 0° C. and stirred. To the mixture was added 1.16 gms. of 2-furoyl chloride and the mixture was stirred overnight. The mixture was then washed with equal volumes of 1M hydrochloric acid, saturated sodium bicarbonate and water. The mixture was then dried over magnesium sulfate and the solvent evaporated to yield 3-benzyloxy-4-methoxyphenyl 2-furoate.

This benzyl protected compound was then deprotected by suspending it in 100 ml of 95% by weight ethanol and then adding 10% by weight palladium on carbon. The mixture was placed on a Parr hydrogenator which was then charged with hydrogen gas to a pressure of approximately 50 lbs/in$^2$. After 3 hours the hydrogen uptake ceased and the mixture was filtered through a Celite pad. The solvent was evaporated to yield 3-hydroxy-4-methoxy-2-furoate. The product was purified by column chromatography. The structure was confirmed employing nuclear magnetic resonance (NMR) methods.

Aqueous solutions were prepared with 0.010 and 0.05 weight percent of the product and it was determined by a panel of experts that the solutions had a sucrose equivalencies of 3 and 4 gms. wt. % respectively.

EXAMPLE II

This example pertains to the making of 3-hydroxy-4-methoxyphenyl 2-thiophenecarboxylate. This compound was prepared by adding 2.00 gms. of 3-benzyloxy-4-methoxyphenol, 1.14 gms. of 2-thiophenecarboxylic acid, and 0.16 gms. of 4-dimethylaminopyridine to 50 ml of methylene chloride which was stirred at 0° C. To the mixture was added 1.90 gms. of dicyclohexylcarbodiimide and the mixture was allowed to warm slowly to room temperature overnight. The mixture was then filtered to remove dicyclohexylurea and the filtrate was washed with 1M hydrochloric acid, saturated sodium bicarbonate, and water. It was then dried over magnesium sulfate, and evaporated to yield the phenol protected product. This was deprotected by dissolving the product in 50 ml of methylene chloride and adding 0.86 gms. of iodotrimethylsilane. After stirring overnight, the reaction was quenched by adding 5 ml. of methanol. After stirring for 30 minutes, the solvent was evaporated and the residue dissolved in ether. This solution was washed with equal volumes of saturated sodium bicarbonate, 1M hydrochloric acid and water, and dried over magnesium sulfate. The solvent was then evaporated and the residue purified by column chromatography to yield 0.3 gms. of 3-hydroxy-4-methoxyphenyl 2-thiophenecarboxylate. The structure was confirmed employing NMR.

To an aqueous solution was added 0.005 weight percent of the product and it was determined by a panel of experts to have a sucrose equivalency of 4 weight percent.

EXAMPLE III

In this example 3-hydroxy-4-methoxyphenyl 3-thiophenecarboxylate was prepared substantially as Example II except that 2.00 gms. of 3-benzyloxy-4-methoxyphenol where coupled with 1.14 gms. of 3-thiophenecarboxylic acid. The structure was confirmed employing NMR.

To an aqueous solution was added 0.01 weight percent of this product and a panel of experts determined it to have a sucrose equivalency of 5.0 weight percent sucrose.

EXAMPLE IV

In this Example 3-hydroxy-4-methoxyphenyl 5-methyl-2-thiophenecarboxylate was prepared substantially as in Example II except that 1.27 gms. of 5-methyl-2-thiophenecarboxylic acid was coupled to 2.00 gms of 3-benzyloxy-4-methoxyphenol. The compound was purified with column chromatography and its structure confirmed using NMR.

An amount of 0.005 weight percent of 3-hydroxy-4-methoxyphenyl 5-methyl-2-thiophenecarboxylate was were added to aqueous solutions and the solutions were determined to have a sucrose equivalency of 3 weight percent sucrose.

EXAMPLE V

In this Example 3-hydroxy-4-methoxyphenyl N-methylpyrrole-2-carboxylate was prepared by adding 1.80 gms of N-methylpyrrole-2-carboxylic acid, 3.00 gms of 3-benzyloxy-4-methoxyphenol and 0.24 gms. 4-dimethylaminopyridine to 50 ml of methylene chloride which was stirred at 0° C. To the mixture was added 2.88 gms. of dicylohexylcarbodimide and the mixture was allowed to warm slowly to room temperature overnight. The mixture was then filtered to remove dicyclohexylurea and the filtrate was washed with 1M hydrochloric acid, saturated sodium bicarbonate and water. It was then dried over magnesium sulfate, and evaporated to yield the phenol protected product. This protected phenol was then suspended in 100 ml of 95% ethanol and 10% palladium on carbon was added. The mixture was placed on a Parr hydrogenator which was then charged with hydrogen to a pressure of about 50 lbs/in$^2$. Upon the cessation of hydrogen uptake the mixture was filtered and the solvent evaporated wherein 1.25 gms. of 3-hydroxy-4-methoxyphenyl N-methylpyrrole-2-carboxylate was prepared. The structure was confirmed using NMR.

To an aqueous solution was added 0.010 weight percent of the purified product and a panel of experts determined it to have a sucrose equivalency of 2 weight percent sucrose.

EXAMPLE VI

In this Example 3-hydroxy-4-methoxyphenyl 3-thienylacetate was prepared substantially as in Example II except that 2.04 gms of 3-thienylacetic acid was coupled to 3.0 gms of 3-benzyloxy-4-methoxyphenol. The structure was confirmed employing NMR.

To an aqueous solution was added 0.005% of the above made product and it was determined to have a sucrose equivalency of 2 percent.

EXAMPLE VII

In this Example 3-hydroxy-4-methoxyphenyl 2-thienylacetate was prepared as described in Example II except that 3 gms of 3-benzyloxy 4-methoxyphenol was coupled to 2.04 gms. of 2-thienylacetic acid. The product structure was confirmed by NMR.

To an aqueous solution was added 0.005 weight percent of this product and was determined to have a sucrose equivalency of 2 weight percent sucrose.

EXAMPLE XVIII

A cherry flavored beverage is prepared by mixing 1.48 gms. of an unsweetened cherry flavored instant beverage base mix with 438 gms. of water, 0.13 gms aspartame (APM) and 0.044 gms. (0.01 weight percent) of 3-hydroxy-4-methoxyphenyl 2-thiophenecarboxylate. The base contains a malic acid and monocalcium phosphate buffer.

EXAMPLE XIX

A mixed fruit gelatin is prepared by mixing 5.16 gms. of unsweetened gelatin base mix with 237 gms. of water, 0.07 gms. (0.029 weight percent) saccharin and 0.024 gms. (0.01 weight percent) of 3-hydroxy-4-methoxyphenyl 2-furoate. The gelatin base contains an adipic acid and disodium phosphate buffer.

EXAMPLE XXIII

A vanilla flavored pudding is prepared by mixing 474 gms. of milk, 21.7 gms. of an unsweetened pudding base mix containing 1.35 gms. of sodium acid pyrophosphate, 36.0 gms. sucrose (6.8 weight percent) and 0.027 gms. (0.005 weight percent) of 3-hydroxy-4-methoxyphenyl 2-thiophenecarboxylate.

What is claimed is:

1. A foodstuff comprising a sweetening compound of the formula:

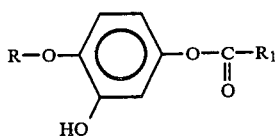

wherein
R is selected from the group consisting of methyl and ethyl;
$R_1$ is selected from the group consisting of

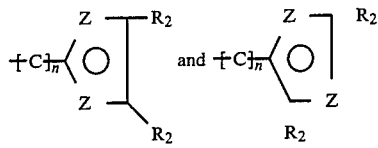

wherein n is an integer from 0 to 1;
each Z is selected from the group consisting of S, O, $NR_2$, N and $CR_2$ with the provisio that at least one Z is a hetero atom and a further provisio that $NR_2$ is not a NH group; and
each $R_2$ is selected from the group consisting of H, $CH_3$, $CH_2CH_3$, $CH_2CH_2CH_3$, $CH(CH_3)_2$, OH, $OCH_3$, $OCH_2CH_3$, $OCH(CH_3)_2$, $CH_2OH$, $CH_2CH_2OH$, $CH_2CHOHCH_3$, $CH_2OCH_3$, CHO, $COCH_3$, $COCH_2CH_3$, $CH_2COCH_3$, COOH and $COOCH_3$ with $R_1$ containing no more than 12 carbon atoms; and salts thereof.

2. A foodstuff according to claim 1 wherein the foodstuff is a beverage.

3. A foodstuff according to claim 1 wherein the foodstuff is a gelatin dessert.

4. A foodstuff according to claim 1 wherein the foodstuff is a milk pudding.

* * * * *